(12) United States Patent
Rakow et al.

(10) Patent No.: US 7,449,146 B2
(45) Date of Patent: Nov. 11, 2008

(54) COLORIMETRIC SENSOR

(75) Inventors: Neal A. Rakow, Woodbury, MN (US); Christopher S. Lyons, St. Paul, MN (US); Stephen P. Maki, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 632 days.

(21) Appl. No.: 10/807,655

(22) Filed: Mar. 24, 2004

(65) Prior Publication Data

US 2004/0184948 A1    Sep. 23, 2004

Related U.S. Application Data

(63) Continuation-in-part of application No. 10/260,369, filed on Sep. 30, 2002, now abandoned.

(51) Int. Cl.
*A01N 1/00* (2006.01)

(52) U.S. Cl. .............................. 422/56; 422/55; 422/58; 436/166

(58) Field of Classification Search ........... 422/50–104; 436/164–172, 518–535; 423/169, 170
See application file for complete search history.

(56) References Cited

U.S. PATENT DOCUMENTS

| | | | |
|---|---|---|---|
| RE24,906 E | | 12/1960 | Ulrich |
| 3,708,296 A | | 1/1973 | Schlesinger |
| 3,723,064 A | * | 3/1973 | Liotta ........................ 436/66 |
| 3,979,184 A | * | 9/1976 | Giaever ...................... 422/57 |
| 4,042,335 A | * | 8/1977 | Clement ..................... 422/56 |
| 4,069,055 A | | 1/1978 | Crivello |
| 4,090,849 A | * | 5/1978 | Healy et al. ................. 422/55 |
| 4,216,288 A | | 8/1980 | Crivello |
| 4,250,311 A | | 2/1981 | Crivello |
| 4,478,942 A | * | 10/1984 | Katsuyama et al. ........... 436/66 |
| 4,558,012 A | * | 12/1985 | Nygren et al. .............. 436/501 |
| 4,601,948 A | | 7/1986 | Lancaster et al. |
| 4,781,890 A | * | 11/1988 | Arai et al. ..................... 422/56 |
| 4,820,649 A | | 4/1989 | Kawaguchi et al. |
| 4,868,288 A | | 9/1989 | Meier |
| 4,877,747 A | * | 10/1989 | Stewart ...................... 436/525 |

(Continued)

FOREIGN PATENT DOCUMENTS

DE          222 419          5/1985

(Continued)

OTHER PUBLICATIONS

Krause et al., "Bicontinuous Nanoporous Polymers by Carbon Dioxide Foaming", *Macromolecules*, vol. 34, pp. 8792-8801 (2001).

(Continued)

*Primary Examiner*—Jill Warden
*Assistant Examiner*—Imran Akram
(74) *Attorney, Agent, or Firm*—Jean A. Lown; James D. Withers (57) ABSTRACT

Colorimetric sensor films comprising a reflective layer, a polymeric detection layer, and a semi-reflective layer are disclosed. Devices comprising the colorimetric sensor films and methods of making the films and devices are also disclosed.

38 Claims, 2 Drawing Sheets

U.S. PATENT DOCUMENTS

| | | | |
|---|---|---|---|
| 4,900,665 A * | 2/1990 | Terashima et al. | 435/21 |
| 4,985,340 A | 1/1991 | Palazzotto et al. | |
| 5,073,476 A | 12/1991 | Meier et al. | |
| 5,084,586 A | 1/1992 | Farooq | |
| 5,122,451 A * | 6/1992 | Tanaka et al. | 435/7.4 |
| 5,124,172 A * | 6/1992 | Burrell et al. | 435/4 |
| 5,124,417 A | 6/1992 | Farooq | |
| 5,218,472 A | 6/1993 | Jozefowicz et al. | |
| 5,393,787 A | 2/1995 | Nestegard et al. | |
| 5,478,527 A * | 12/1995 | Gustafson et al. | 422/82.11 |
| 5,512,650 A | 4/1996 | Leir et al. | |
| 5,514,728 A | 5/1996 | Lamanna et al. | |
| 5,611,998 A | 3/1997 | Aussenegg et al. | |
| 5,639,671 A | 6/1997 | Bogart et al. | |
| 5,670,006 A | 9/1997 | Wilfong et al. | |
| 5,721,289 A | 2/1998 | Karim et al. | |
| 5,869,272 A * | 2/1999 | Bogart et al. | 435/7.32 |
| 5,877,895 A | 3/1999 | Shaw et al. | |
| 5,882,774 A | 3/1999 | Jonza et al. | |
| 6,007,904 A | 12/1999 | Schwotzer et al. | |
| 6,010,751 A | 1/2000 | Shaw et al. | |
| 6,045,756 A * | 4/2000 | Carr et al. | 422/82.11 |
| 6,180,318 B1 | 1/2001 | Fitzer et al. | |
| 6,264,747 B1 | 7/2001 | Shaw et al. | |
| RE37,412 E | 10/2001 | Aussenegg et al. | |
| 6,296,927 B1 | 10/2001 | Jonza et al. | |
| 6,312,888 B1 | 11/2001 | Wong et al. | |
| 6,327,031 B1 * | 12/2001 | Gordon | 356/72 |
| 6,396,616 B1 | 5/2002 | Fitzer et al. | |
| 6,492,133 B1 * | 12/2002 | Wickert et al. | 435/34 |
| 6,613,421 B2 | 9/2003 | Jonza et al. | |
| 6,635,337 B2 | 10/2003 | Jonza et al. | |
| 6,664,306 B2 | 12/2003 | Gaddam et al. | |
| 7,153,651 B1 * | 12/2006 | Drewes et al. | 435/6 |
| 2001/0048072 A1 | 12/2001 | Painchaud et al. | |
| 2002/0168295 A1 * | 11/2002 | Cunningham et al. | 422/82.05 |
| 2003/0207454 A1 * | 11/2003 | Eyster et al. | 436/8 |
| 2004/0184948 A1 | 9/2004 | Rakow et al. | |

FOREIGN PATENT DOCUMENTS

| | | |
|---|---|---|
| DE | 38 32 185 | 3/1990 |
| EP | 094914 | 11/1983 |
| EP | 109851 | 5/1984 |
| EP | 0 395 300 | 10/1990 |
| EP | 0 665 425 | 8/1995 |
| EP | 0 979 994 | 2/2000 |
| WO | WO 87/03837 | 10/1984 |
| WO | WO 89/06284 | 7/1989 |
| WO | WO 01/21693 | 3/2001 |
| WO | WO 2004/031760 | 4/2004 |
| WO | WO 2005/042771 | 5/2005 |
| WO | WO 2005/111588 | 11/2005 |

OTHER PUBLICATIONS

Walheim et al., "Nanophase-Separated Polymer Films as High-Performance Antireflection Coatings", *Science*, vol. 283, p. 520 (1999).

Budd et al., "Polymers of Intrinsic Microporosity (PIMs): Robust, Solution-Processable, Organic Nanoporous Materials", *Chem. Comm.*, pp. 230-231 (2004).

G. Odian, "Principles of Polymerization" Third Edition, John Wiley & Sons Inc., pp. 532-603. New York (1991).

"Encyclopedia of Polymer Science and Engineering", Second Edition, H.F. Mark, N. M. Bikales, C.G. Overberger, G. Menges, J. I. Kroschwitz, Eds., vol. 2, 729-814 (1985) John Wiley & Sons, New York.

"Encyclopedia of Polymer Science and Technology", 6, 322 (1986).

* cited by examiner

COLORIMETRIC SENSOR

RELATED APPLICATIONS

This application is a continuation-in-part patent application of U.S. patent application Ser. No. 10/260,369 filed on Sep. 30, 2002 now abandoned.

TECHNICAL FIELD OF THE INVENTION

This disclosure relates to colorimetric sensor films.

BACKGROUND OF THE INVENTION

The development of robust chemical sensors for a range of analytes remains an important endeavor for applications such as environmental monitoring, product quality control, and chemical dosimetry. Among the many methods available for chemical sensing, calorimetric techniques remain advantageous in that the human eye can be used for signal transduction, rather than extensive instrumentation.

Though colorimetric sensors currently exist for a range of analytes, most are based upon employing dyes or colored chemical indicators for detection. Such compounds are typically selective, meaning arrays are necessary to enable detection of various classes of compounds. Moreover, many of these systems have lifetime limitation issues, due to photobleaching or undesirable side reactions. Other optical sensing techniques, such as surface plasmon resonance and spectral interferometry, require substantial signal transduction hardware to provide response, and thus are not useful for simple visual indication.

SUMMARY OF THE INVENTION

The present invention features novel multi-layered colorimetric sensor films. The films typically constitute a highly colored multi-layered interference filter whose hue shifts upon analyte exposure. The multi-layered structure provides a versatile platform for incorporating a variety of chemistries that can detect a range of species. The films are flexible and robust, and can be designed to provide fast, reversible (or, in some cases, permanent) responses. As such, they are well-suited for application to the areas mentioned above.

The colorimetric sensors of the present invention may comprise a reflective layer, a detection layer over the reflective layer, and a semi-reflective layer over the detection layer. Additional layers may also be present in the colorimetric sensors of the present invention as long as the additional layers do not negatively impact the ability of the sensor to detect a given analyte. When present, additional layers may be present between any of the above-mentioned layers (i.e., the reflective layer, the detection layer, and the semi-reflective layer) and/or on either side of the reflective layer and/or the semi-reflective layer.

A variety of layer configurations and materials may be used to form the colorimetric sensors of the present invention. For example, the reflective layer of the colorimetric sensor may be a substantially continuous layer or a discontinuous layer, and may comprise one or more individual layers. The detection layer may comprise a single or multiple layers containing (i) at least one polymer component, (ii) at least one inorganic component, or (iii) a combination of (i) and (ii). In addition, like the reflective layer, the semi-reflective layer may be a substantially continuous layer or a discontinuous layer, and may comprise one or more individual layers. The construction and composition of the colorimetric sensors of the present invention will vary depending on a number of factors including, but not limited to, the analyte or analytes of interest, the medium containing the analyte or analytes, and the desired sensitivity of the sensor.

In one exemplary embodiment, the present invention is directed to a colorimetric sensor for measuring one or both of the presence and concentration of an analyte comprising a substantially continuous reflective layer; a detection layer over the reflective layer, the detection layer comprising at least one polymer component, said detection layer being capable of a change in optical thickness upon exposure to said analyte; and a substantially continuous semi-reflective layer over the detection layer, the semi-reflective layer having an index of refraction different from the index of refraction of the detection layer, wherein at least a portion of the semi-reflective layer is permeable to said analyte.

In a further exemplary embodiment, the present invention is directed to a colorimetric sensor for measuring one or both of the presence and concentration of an analyte comprising a substantially continuous reflective layer; a detection layer over the reflective layer, the detection layer comprising at least one polymer component; and a substantially continuous semi-reflective layer over the detection layer, the semi-reflective layer having an index of refraction different from the index of refraction of the detection layer, said sensor being capable of a change in color upon exposure to said analyte.

In yet a further exemplary embodiment, the present invention is directed to a colorimetric sensor for measuring one or both of the presence and concentration of an analyte, wherein the colorimetric sensor comprises a substantially continuous reflective layer; a detection layer over the reflective layer, the detection layer comprising (i) at least one polymer component, (ii) at least one inorganic component, or (iii) both (i) and (ii); and a substantially continuous semi-reflective layer over the detection layer, the semi-reflective layer having an index of refraction different from the index of refraction of the detection layer and being permeable to said analyte, said sensor being capable of a change in color upon exposure to said analyte.

In even a further exemplary embodiment, the present invention is directed to a colorimetric sensor for measuring one or both of the presence and concentration of an analyte, wherein the colorimetric sensor comprises a reflective layer; a detection layer over the reflective layer; and a discontinuous semi-reflective layer over the detection layer, the semi-reflective layer having an index of refraction different from the index of refraction of the detection layer, said sensor being capable of a change in color upon exposure to said analyte. In this embodiment, the sensor desirably has at least one of the following features: (a) the discontinuous semi-reflective layer comprises a single layer of semi-reflective islands having at least one dimension greater than 10 µm, and exposed areas between the semi-reflective islands, said exposed areas having a width of at least 1.0 µm; (b) the discontinuous semi-reflective layer comprises a single layer of semi-reflective islands and the detection layer contains wells extending a depth into the detection layer; (c) the discontinuous semi-reflective layer comprises a single layer of semi-reflective islands and the detection layer comprises at least one inorganic component either alone or in combination with at least one polymer component; (d) the detection layer comprises at least one inorganic component, wherein said at least one inorganic component is (i) blended with at least one polymer component, (ii) within a given layer containing at least one polymer component but not blended with the at least one polymer component, (iii) in a layer separate from a layer containing at least one polymer component, or (iv) any combination of (i) to (iii); and (e) the detection layer comprises at least two different polymeric components, wherein the polymeric components are (1) blended with one another, (2) within a given layer but not blended with one another, (3) in a layer separate from one another, or (4) any combination of (1) to (3).

The present invention is further directed to arrays of sensors. One or more similar or different colorimetric sensors of the present invention may be combined to form an array of sensors capable of providing a composite signal to a user upon exposure to one or more analytes. Such composite signals can provide additional information, such as the identity of a pure analyte or a mixture of analytes, relative to a signal produced by a single colorimetric sensor.

The present invention is even further directed to a device comprising a colorimetric sensor and a light source, a housing component, or a combination thereof.

The present invention is also directed to a method of detecting the presence or absence of an analyte comprising providing a colorimetric sensor (or array of sensors) as described above, providing a light source, contacting the sensor (or array of sensors) with a medium that may contain an analyte, and monitoring the sensor (or array of sensors) for a change in optical properties.

As used in this invention:

"analyte" means the specific component that is being detected in a chemical or biochemical analysis;

"dimensional change" means a change of distance in a direction normal to the surface of the detection layer surface;

"porous material" means a material containing a continuous network of pores throughout its volume;

"reflective" means semi-reflective or fully reflective;

"semi-reflective" means neither fully reflective nor fully transmissive, preferably about 30 to about 70% reflective, more preferably about 40 to about 60% reflective.

"substantially continuous" means a layer of material is non-porous, but may have cracks, grain boundaries, or other structures that create pathways through the layer of material. A "substantially continuous" layer may be non-porous, but permeable to one or more analytes.

"discontinuous" means a layer of material having at least two separate and distinct islands with empty space therebetween, wherein the at least two separate and distinct islands with empty space therebetween are within a given plane.

An advantage of at least one embodiment of the present invention is that the multi-layer sensor films can be constructed so that water vapor does not create a change in the optical properties.

Another advantage of at least one embodiment of the present invention is that the films can be readily processed. The reflective layers can be deposited via evaporative or sputter coating, while the detection layer can be deposited via solvent coating, plasma deposition, and vapor coating (as described in U.S. Pat. No. 5,877,895).

Another advantage of at least one embodiment of the present invention is that the change in appearance of the sensor can be designed to be reversible or permanent.

Other features and advantages of the invention will be apparent from the following drawings, detailed description, and claims.

DETAILED DESCRIPTION OF THE INVENTION

The multi-layered colorimetric sensor films of the present invention may comprise colored films containing at least one polymeric detection layer between a reflective and a semi-reflective layer, which may both be metal layers. These multi-layered films provide a general means for visual signal transduction. The films function as interference filters, and thus can be highly colored due to reflection of particular wavelengths within the visible range. The coloration of the sensor films is highly dependent upon the thickness of each layer within the stack.

Figure 1:
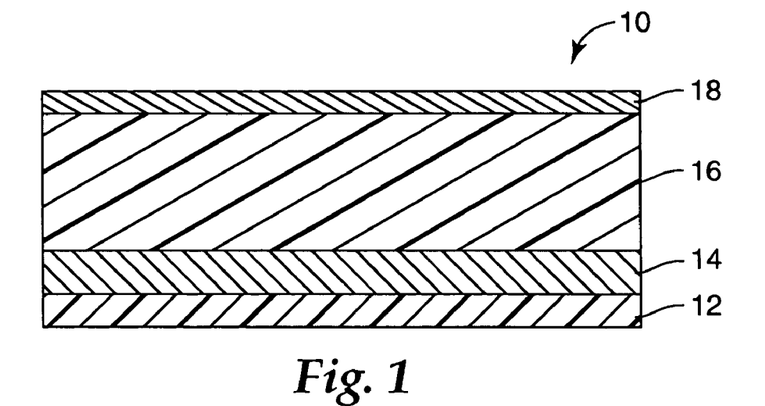
FIG. 1 depicts an exemplary multi-layered film of the present invention.

A general depiction of a multi-layered sensor film of the present invention is shown in FIG. 1. In general, exemplary multi-layered film sensor 10 comprises (optional) substrate layer 12, reflective layer 14, detection layer 16, and semi-reflective layer 18.

The sensor films can be used for detecting the presence and/or concentration of an analyte or of a mixture of analytes. The analyte may be a gas (e.g., a vapor) or a liquid. The analyte can be a molecule, a macromolecule, a biomolecule, or a biomacromolecule. The analyte may be present in a gaseous medium (such as air) or liquid medium (such as water or other fluids). Typically the analyte is an organic material.

In at least one embodiment, the analyte is detected by a change in optical thickness of a polymer comprising a detection layer upon exposure to the analyte. The analyte passes through an outer semi-reflective layer and changes the optical thickness of the detection layer. In one embodiment the analyte is absorbed into at least a portion of the detection layer. Upon absorption, color changes (often vivid) can indicate the presence of the analyte.

The change in optical thickness is typically observable in the visible light range and can be detected by the unaided human eye. However, sensors can be designed to show a change in optical thickness when subjected to other light sources such as UV, infrared, or near infrared. Various detection mechanisms can also be used. Examples of suitable detection mechanisms include spectrophotometers, fiber optic spectrophotometers, and photo-detectors, e.g., charge coupled devices (ccd), digital cameras, etc.

In another embodiment, the analyte is detected when its presence causes the delamination of the detection layer from an adjacent layer. Typically, delamination occurs when the analyte wets the interface of the detection layer and an adjacent layer, thereby reducing the interface adhesion. When delamination occurs, optical interference is destroyed and the sensor loses perceptible color. The presence of the analyte may also cause dewetting of one or more polymers within the detection layer from an adjacent layer. This process, which involves changes in the shape of the detection layer that reduce the interfacial area with adjacent layers, causes defects within the material which permanently change the optical properties of the sensor film.

Substrate

The substrate is optional, but when present it may comprise any suitable material capable of providing support for the colorimetric sensor. It may be flexible or non-flexible. The substrate material can be tailored to the application. Preferably, it is suitable to use in a vacuum deposition process.

Reflective Layer

The reflective layer may comprise any material that can form a fully reflective or semi-reflective layer. It is preferable that the material is fully reflective at a thickness of about 20 to about 200 nm. Thinner layers can typically be used to make the reflective layer semi-reflective. Although the reflective layer is typically made to be more reflective than the semi-reflective layer, sometimes it is desirable to have the reflectivity of the reflective layer and semi-reflective layer be the same so a response to the presence of an analyte can be seen from either side of the sensor film.

Suitable materials for the reflective layer include metals or semi-metals such as aluminum, chromium, gold, nickel, silicon, and silver. Other suitable materials that may be included in the reflective layer include metal oxides such as chromium oxide and titanium oxide.

In some exemplary embodiments of the present invention, the reflective layer is at least about 90% reflective (i.e., at least about 10% transmissive), and in some embodiments, about 99% reflective (i.e., about 1% transmissive). In other exemplary embodiments of the present invention, the reflective layer is a semi-reflective layer, wherein the reflective layer is at least about 20% reflective, such as about 20 to about 90% reflective, or about 30 to about 70% reflective.

In some embodiments, the reflective layer also acts as the substrate, providing support for the sensor. The reflective layer may be a substantially continuous layer or a discontinuous layer. Further, the reflective layer may comprise one or more reflective layers. Desirably, the reflective layer comprises a single reflective layer.

Detection Layer

The detection layer may comprise one or more polymers or copolymers. In most embodiments, the detection layer comprises at least one polymer whose optical thickness changes upon exposure to an analyte. The change in optical thickness can be caused by a dimensional change such as a change in physical thickness of the polymer due to swelling or shrinkage or a change in refractive index of the detection layer due to the presence or chemical reaction of the analyte. The detection layer may change from one color to another, from a color to no color, or from no color to a color.

Like the reflective layer, the detection layer may comprise one or more layers. The detection layer may also comprise two or more sub-layers. One or more of the sub-layers may be discontinuous or patterned. The sub-layers typically comprise different polymeric materials and may absorb different analytes and/or may have different degrees of sensitivity to one or more analytes. The sub-layers may have a variety of configurations. For example, the sub-layers may be stacked to form a stack of two or more layers or may be positioned within the same layer in a side-by-side configuration.

The detection layer may comprise a pattern so as to create colored images, words, or messages upon exposure to an analyte. A sublayer may be patterned by having one or more portions that are reactive to a particular analyte and one or more portions that are non-reactive to the same analyte. Alternatively, a pattern of reactive material may be deposited on a larger non-reactive sublayer. In this case, it is preferable to make the patterned layer very thin so that no difference in optical thickness is apparent until an analyte is absorbed. The patterning can provide easily identifiable warnings for a user upon exposure to an analyte.

The thickness of the detection layer may be patterned, for example, as described in U.S. Pat. No. 6,010,751. This may be desirable when the sensor is designed so that the presence of an analyte causes the detection layer to swell or shrink, thereby making a pattern disappear (for example when a thinner portion swells to the same thickness as a thicker portion) or appear (for example, when an portion shrinks to a thinner thickness than an adjacent portion). Patterns may also be made to appear by starting with thinner and thicker regions that appear the same color initially, but, when exposed to one or more analytes, one or both of the thinner and thicker regions swell to give two different hues.

The detection layer may comprise a blend of polymer components. The blend may be homogeneous or heterogeneous. A blend of polymer components in the detection layer can allow for a large number of analytes to be detected with the use of a relatively small sensor. In one exemplary embodiment of the present invention, the detection layer comprises at least two different polymeric components, wherein the polymeric components are (1) blended with one another, (2) within a given layer but not blended with one another (i.e., in a side-by-side configuration), (3) in a layer separate from one another (i.e., in a stack), or (4) any combination of (1) to (3).

The detection layer may be porous. In other words, the detection layer may contain a continuous network of pores throughout its volume. This can boost the sensitivity of detection due to the increase in surface area exposed to an analyte and/or the propensity of pores to condense vaporous analytes. Porosity can be obtained by using porous materials such as foams made from high internal phase emulsions, such as those described in WO 01/21693, to form the detection layer. Porosity may also be obtained via carbon dioxide foaming to create bi-continuous, nanoporous material (see "Macromolecules", 2001, vol. 34, pp. 8792-8801), or by nanophase separation of polymer blends (see "Science", 1999, vol. 283, p. 520). In general, the pore diameters need to be smaller than the wavelength of the light source used in the detection process. Typically, pores having an average pore size of 10 nm or less are desired within the detection layer.

In one embodiment of the present invention, polymers having an intrinsic microporosity, or PIMs, may also be used to form the detection layer. As used herein, "polymers having an intrinsic microporosity," or "PIMs," refer to non-network polymers that form microporous solids due to their highly rigid and contorted molecular structures. Because of their molecular structure, the PIMs are unable to fill space efficiently, resulting in a microporous structure (e.g., a structure that typically contains pores having an average pore size of less than about 2 nm). Suitable polymers of intrinsic microporosity (PIMs) include, but are not limited to, polymers disclosed in "Polymers of intrinsic microporosity (PIMs): robust, solution-processable, organic nanoporous materials," Budd et al., *Chem. Commun.*, 2004, pp. 230-231, the subject matter of which is incorporated herein by reference in its entirety.

One or more polymers within the detection layer may be at least partially crosslinked. Crosslinking may be desirable in some embodiments because it can increase mechanical stability and sensitivity to certain analytes. Crosslinking can be achieved by incorporating one or more multi-functional monomers into the detection layer, or by subjecting the detection layer to, e.g., electron beam or gamma ray treatment. In one desired embodiment of the present invention, crosslinking is done in the presence of a porogen, which may be subsequently extracted from the crosslinked system to yield a porous detection layer. Suitable porogens include, but are not limited to, inert organic molecules, such as normal alkanes (e.g., decane) or aromatics (e.g., benzene, toluene).

For many applications, it is desirable that the polymer or copolymer be hydrophobic. This will reduce the chance that water vapor (or liquid water) will cause a change in optical thickness of the polymer and interfere with the detection of an analyte, for example, in the detection of organic solvent vapors.

For the detection of organic solvent vapors, polymeric materials suitable for the detection layer include, but are not limited to, polymers and copolymers (including block copolymers) prepared from classes of monomers including hydrophobic acrylates and methacrylates, difunctional monomers, vinyl monomers, hydrocarbon monomers (olefins), silane monomers, and fluorinated monomers.

Examples of hydrophobic acrylates and methacrylates include, but are not limited to, n-alkyl(meth)acrylates having alkyl groups —$C_xH_{2x}CH_3$ wherein x is from 1 to about 17, methyl(meth)acrylate, isodecyl(meth)acrylate, 2-ethylhexyl (meth)acrylate, cyclohexyl(meth)acrylate, n-decyl(meth) acrylate, n-butyl(meth)acrylate, isooctyl(meth)acrylate, isopropyl(meth)acrylate, lauryl(meth)acrylate, ethyl(meth) acrylate, adamantyl(meth)acrylate, t-butyl(meth)acrylate, 2-phenoxyethyl(meth)acrylate, isobornyl(meth)acrylate, and poly(dimethylsiloxane)mono(meth)acrylate.

Examples of multi-functional monomers include, but are not limited to, divinylbenzene, ethyleneglycol di(meth)acrylate, diethyleneglycol di(meth)acrylate, triethyleneglycol di(meth)acrylate, tetraethylene glycol di(meth)acrylate, tripropylene glycol di(meth)acrylate, polyethylene glycol di(meth)acrylate 1,6-hexanedioldi(meth)acrylate, trimethylol propane di(meth)acrylate, neopentyl glycol di(meth)acrylate, N,N-methylenebis(meth)acrylamide, poly(dimethylsiloxane)di(meth)acrylate, poly(ethyleneglycol)di(meth) acrylate, diacrylates such as those commercially available from UCB Chemicals under the trade designation "IRR 214", pentaerythritol tri- and tetra-acrylate, and trimethylol propane tri(meth)acrylate.

Examples of vinyl monomers include, but are not limited to, styrene, α-methylstyrene, vinylacetate, vinylbutyrate, vinylstearate, vinylchloride, and vinyl norbornene.

Examples of hydrocarbon monomers (olefins) include, but are not limited to, isobutylene, ethylene, propylene, butadiene, and norbornene.

Examples of silane monomers include, but are not limited to, organohydrosilanes, alkoxysilanes, phenoxysilanes, and fluoroalkoxysilanes.

Examples of fluorinated monomers include, but are not limited to, tetrafluoroethylene, vinylidene fluoride, hexafluoropropylene, and perfluoroalkyl(meth)acrylates.

For detection in solution, detection of highly polar analytes, and/or use in sensor arrays polymeric materials suitable for the detection layer include, but are not limited to, polymers and copolymers (including block copolymers) prepared from classes of monomers including hydroxylated monomers, acrylamides, anhydrides, aldehyde-functionalized monomers, amine or amine salt functionalized monomers, acid functionalized monomers, epoxide functionalized monomers, vinyl monomers, the multifunctional monomers listed above, and other polymers.

Examples of hydroxylated monomers include, but are not limited to, hydroxyalkyl(meth)acrylates, hydroxyethyl (meth)acrylate, and hydroxymethyl(meth)acrylate.

Examples of acrylamides and acrylonitriles include, but are not limited to, (meth)acrylamide, N-isopropyl(meth) acrylamide, N,N-dimethyl(meth)acrylamide, and (meth) acrylonitrile.

Examples of anhydrides include, but are not limited to, (meth)acrylic anhydride and maleic anhydride.

Examples of aldehyde-functionalized monomers include, but are not limited to, acrolein.

Examples of amine or amine salt functionalized monomers include, but are not limited to, t-butylaminoethyl(meth)acrylate, diisopropylaminoethyl(meth)acrylate, dimethylaminoethyl(meth)acrylate, vinylpyridine, dimethylaminoethyl (meth)acrylate-methyl chloride salt, aminostyrene, 4-aminostyrene, and vinylimidazole.

Examples of acid functionalized monomers include, but are not limited to, (meth)acrylic acid, carboxyethyl(meth) acrylate, (meth)acrylic acid-metal salts, styrene sulfonic acid, monomers commercially available from UCB Chemicals under the trade designation "EBECRYL 170" from UCB Chemicals, vinylphosphonic acid, and vinylsulfonic acid.

Examples of epoxide functionalized monomers include, but are not limited to, glycidyl(meth)acrylate.

Examples of vinyl monomers include, but are not limited to, N-vinylpyrrolidone, vinyldimethylazalactone (VDM), vinylidene chloride, vinylalcohol, and vinylphenol.

Examples of other polymers include, but are not limited to, poly(ethyleneoxide), poly(caprolactone), poly(sulfone), poly (ethyleneglycol), poly(urethanes), poly(carbonate), poly(ethyleneimine), poly(vinyl alcohol), poly(vinylphenol), ethyl cellulose, fluoropolyol, polyesters, polyamides, polyimides, and polyacetals. The polymer component(s) of the detection layer may also have appropriate functional groups or molecular receptors incorporated to detect specific analytes. For example, acid-functionalized polymers, such as poly(acrylic acid), enable detection of organic bases such as ammonia gas. Incorporation of metal complexes, such as metalloporphyrins, within the detection layer enables detection of ligating species such as phosphines or mercaptans. Suitable molecular receptors include, but are not limited to, calixarenes, cyclodextrins, dendritic polymers, carbon nanotubes, azacrowns, crown ethers, anion chelating agents containing Lewis acid functionality, organometallic metal complexes, porphyrins, metalloporphyrins, peptides, glycopeptides, proteins, antibodies, enzymes, oligonucleotides, and nucleic acids.

In a further embodiment of the present invention, the detection layer comprises one or more inorganic materials alone or in combination with one or more of the above-described polymeric materials. In one exemplary embodiment of the present invention, the detection layer comprises one or more inorganic materials without polymeric material. In a further exemplary embodiment, the detection layer comprises one or more inorganic materials in combination with one or more of the above-described polymeric materials. In embodiments containing both inorganic material and polymeric material, the inorganic materials may be present as a distinct layer within the detection layer or may be intermixed with polymeric material to form a single layer. Further, the inorganic materials may be present as a distinct layer within the detection layer separate from one or more polymeric layers (i.e., in a stack of polymeric layers and inorganic layers) or may be within a single layer along with polymeric material but not intermixed with the polymeric material (i.e., a side-by-side configuration having a distinct section of inorganic material and a distinct portion of polymeric material).

Suitable inorganic materials for use in the detection layer include, but are not limited to, transparent and porous metal oxides, nitrides, and oxynitrides of appropriate thickness for producing color by optical interference. Specific examples of suitable inorganic materials include, but are not limited to, silicon oxides, silicon nitrides, silicon oxynitrides, aluminum oxides, titanium oxides, titanium nitride, titanium oxynitride, tin oxides, zirconium oxides, and combinations thereof. Other inorganic materials, such as zeolites, are also suitable for use in the detection layer. Desirably, the inorganic material is a porous material as defined above.

In one embodiment of the present invention, inorganic materials are used as "analyte sorptive materials" or "analyte reactive materials" within the detection layer. In this embodiment, inorganic materials, such as those described above, may be used alone or may be used as a base substrate having analyte-reactive or analyte-sorptive groups bonded thereto. For example, particulate metal oxides, nitrides, and/or oxynitrides having an organosilane compound bonded thereto may be distributed throughout the detection layer.

By incorporating the appropriate chemistries and/or analyte receptor moieties within the detection layer, it should be feasible to create sensors for a wide range of analytes in solution. Either by initial deposition or by post-functionalization of deposited materials, receptor molecules, such as peptides or antibodies, may potentially be covalently linked to the polymer. In such fashion, biosensors for selective detection of bacteria, proteins, ions, etc. could be fabricated.

The detection layer can have any desired overall thickness. Desirably, the detection layer has an overall thickness of more than about 50 nm, such as in the range of about 100 to about 1000 nm. In one embodiment of the present invention, the detection layer has a layer thickness that is substantially the same throughout the detection layer. See, for example, detection layer 16 of FIG. 1. In other embodiments of the present invention, the detection layer has a layer thickness that varies from a first location within the detection layer to one or more other locations within the detection layer. In either case, the semi-reflective layer applied over the detection layer may be applied so as to conform to the thickness variations in the detection layer.

Figure 2:
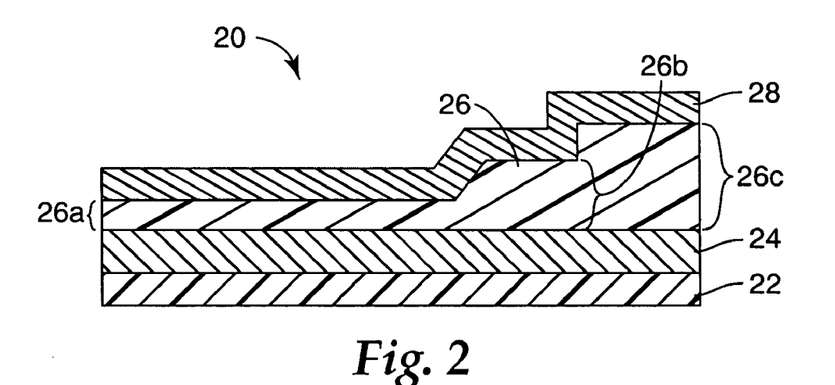
FIG. 2 depicts an exemplary multi-layered film of the present invention containing a detection layer that varies in thickness from one location to another.

An exemplary sensor of the present invention containing a detection layer that varies in thickness from one location to another is shown in FIG. 2. As shown in FIG. 2, sensor 20 comprises (optional) substrate layer 22, reflective layer 24, detection layer 26, and semi-reflective layer 28. Detection layer 26 has a first thickness, $t_{26a}$, at first location 26a, a second thickness, $t_{26b}$, at second location 26b, and a third thickness, $t_{26c}$, at third location 26c. In exemplary sensor 20, although the layer thickness of detection layer 26 varies throughout detection layer 26, the thickness of semi-reflective layer 28 remains substantially constant.

In one exemplary embodiment of the present invention, the detection layer comprises one or more "wells" positioned within the detection layer. As used herein, the term "wells" is used to describe holes, grooves, channels, or any other voids (other than pores) within the detection layer. Unlike pores, wells do not form a continuous network throughout the detection layer volume. Typically, wells extend from an upper surface of the detection layer (i.e., below the semi-reflective layer) into the detection layer a given depth. Wells typically have at least one dimension (i.e., length, width, or diameter) of less than about 10 nm; however, any well size may be used in the present invention. In one desired embodiment of the present invention, the wells have at least one dimension (i.e., length, width, or diameter) ranging from about 1.0 to about 10 nm, more desirably, about 5 nm. In some embodiments of the present invention, the wells have at least one dimension (e.g., width) ranging from about 1.0 to about 10 nm, and at least one other dimension (e.g., length) much greater than 5 nm, such as a dimension ranging from greater than 10 nm to the width of the detection layer. An exemplary sensor of the present invention containing wells within the detection layer is shown in FIG. 3.

Figure 3:
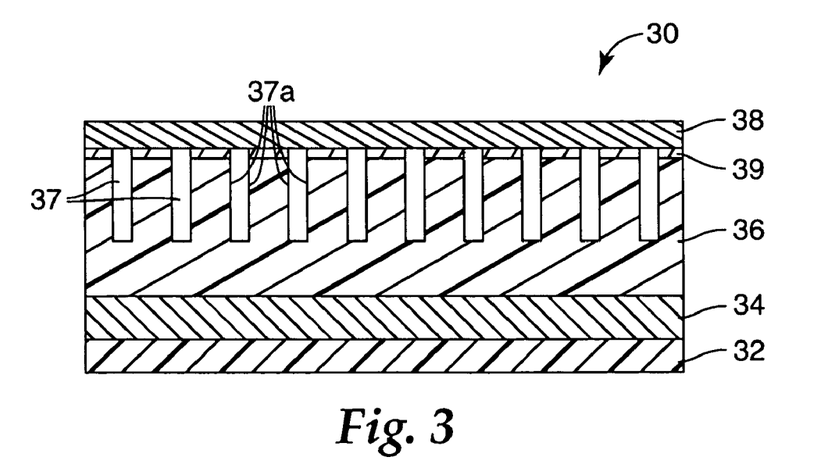
FIG. 3 depicts an exemplary multi-layered film of the present invention having a substantially continuous semi-reflective layer and wells in the detection layer.

As shown in FIG. 3, exemplary multi-layered film sensor 30 comprises (optional) substrate layer 32, reflective layer 34, detection layer 36 having wells 37 therein, and semi-reflective layer 38 over detection layer 36 and wells 37. In this embodiment, detection layer 36 has an increased surface area due to surface areas 37a along inner surfaces of wells 37. The degree of increased surface area within detection layer 36 may be controlled by varying one or more of the following parameters: the number of wells 37 per given area, the depth of each well 37, and the volumetric size of each well 37.

Wells, when present, may be present as random voids within the detection layer or in the form of a pattern distributed within the detection layer, wherein the wells extend a desired depth into the detection layer. When the detection layer contains one or more wells, the wells may be provided using a variety of techniques. One suitable method for providing wells within the detection layer comprises an etching method as described in Example 10 below. In this exemplary method, a reflective layer is first coated onto a temporary or permanent carrier. A detection layer, such as a polymeric detection layer, is then coated onto the reflective layer. Then a metal, such as Cr, is coated onto the detection layer in "island" form (i.e., a pattern of metal islands and uncoated areas). The size and density of the islands on the detection layer may be controlled by the placement of a screen between the metal (i.e., Cr) source and the detection layer. Then, oxygen plasma in Reactive Ion Etch (RIE) mode is used to etch the detection layer in uncoated areas. The metal (e.g., Cr) islands serve as an etch mask, and are converted to a transparent oxide, such as $CrO_x$, during the etching step (see, for example, layer 39 in FIG. 3).

The above-described exemplary etching process produces nanometer-dimensioned wells between the transparent oxide islands. Typically, the transparent oxide islands are uniformly dispersed over an upper surface of the detection layer and have at least one dimension (i.e., length, width, or diameter) of less than about 100 nm; however, any transparent oxide island size, shape, and density may be used in the present invention.

Wells 37 may extend into detection layer 36 at any depth as desired for a given application. As shown in FIG. 3, wells 37 may extend into detection layer 36 and end at some point within detection layer 36. In other embodiments, wells 37 may extend through detection layer 36 to reflective layer 34 (see FIG. 3).

Once the etching step is completed, a semi-transparent layer (or other layer) may be coated over the transparent oxide islands and wells, such as semi-transparent layer 38 shown in FIG. 3. In this embodiment, color-shifting interference results in the appearance of a single uniform color, which varies with a given viewing angle. Alternatively, the transparent oxide islands (i.e., layer 39 shown in FIG. 3) may be removed prior to applying the semi-transparent layer over the detection layer "islands" and wells positioned between the "islands."

Semi-Reflective Layer

The semi-reflective layer may comprise any material that can form a permeable, semi-reflective layer and has a different index of refraction than the detection layer. In most embodiments, it is preferable that the material is semi-reflective at a thickness of about 5 nm because at this thickness most analytes will be able to permeate through this layer to the detection layer. Desired thicknesses will depend on the material used to form the layer, the analyte to be detected, and the medium that will carry the analyte.

Suitable materials include metals and semi-metals such as aluminum, chromium, gold, nickel, silicon, and silver. Other suitable materials that may be included in the semi-reflective layer include oxides such as aluminum oxide, titanium oxide, and chromium oxide.

Like the reflective layer, the semi-reflective layer may be a substantially continuous layer or a discontinuous layer. Further, like the reflective layer, the semi-reflective layer may comprise one or more semi-reflective layers. Desirably, the semi-reflective layer comprises a single semi-reflective layer, which is either substantially continuous or discontinuous.

In one exemplary embodiment of the present invention, the semi-reflective layer is a substantially continuous layer. In this embodiment, the construction and composition of the semi-reflective layer may be substantially consistent across an upper surface of and throughout the semi-reflective layer. Alternatively, the construction and/or composition of the semi-reflective layer may vary across an upper surface of and throughout the semi-reflective layer. For example, the semi-reflective layer may have a differential permeability such that the semi-reflective layer has higher analyte permeability for a given analyte at a first location on an upper surface of the semi-reflective layer and lower analyte permeability for the same analyte at a second location on the upper surface. The first and second locations on the upper surface of the semi-reflective layer may be randomly positioned relative to one another, or may form a pattern on the upper surface.

The substantially continuous semi-reflective layer may also have a pattern therein wherein first regions of the semi-reflective layer have a greater light reflectance than second regions of the semi-reflective layer. The first and second regions on the semi-reflective layer may form a pattern on the upper surface of and within the semi-reflective layer. Like the patterned detection layer described above, a patterned semi-reflective layer may comprise a pattern so as to create colored images, words, or messages upon exposure of the underlying detection layer to an analyte. The semi-reflective layer can provide easily identifiable warnings for a user upon exposure to an analyte.

Any number of methods may be used to alter the permeability of the semi-reflective layer and/or create a pattern on and within the semi-reflective layer. Suitable methods include, but are not limited to, spatially controlling the deposition conditions of the semi-reflective layer to vary the thickness or density of the semi-reflective layer. For example, a mask can be placed between the deposition source and the substrate such that the thickness of deposited semi-reflective layer varies from a first location to a second location on an upper surface. The differential permeability and/or creation of a pattern on and within the semi-reflective layer can also be produced by post-treatment of the semi-reflective layer with localized energy inputs such as laser treatment to change the microstructure of the semi-reflective layer.

Any of the above-mentioned methods may be used to create one or more patterns on the semi-reflective layer. The choice of a given pattern or patterns may depend on a number of factors including, but not limited to, the analyte or analytes of interest, the semi-reflective material or materials used, the message, if any, displayed to a user, or a combination thereof.

Exemplary multi-layered films of the present invention having a substantially continuous semi-reflective layer are shown in FIGS. 1-3. In one exemplary multi-layered film sensor of the present invention, the multi-layered film sensor comprises a substantially continuous semi-reflective layer over a detection layer, wherein the detection layer has an increased surface area for potentially enhanced detection of an analyte due the presence of one or more wells within the detection layer (see FIG. 3). Desirably, the substantially continuous semi-reflective layer positioned over the detection layer containing wells is a single layer of semi-reflective material.

In a further exemplary embodiment of the present invention, the semi-reflective layer is a discontinuous layer. In this embodiment, the composition of the semi-reflective layer may be substantially consistent across the semi-reflective layer; however, areas separate the semi-reflective layer into two or more discontinuous regions. The discontinuous semi-reflective layer may comprise any pattern of semi-reflective islands within a "sea" of exposed areas (i.e., the detection layer is exposed). The size and density of semi-reflective islands on the detection layer may vary as desired, and may be uniformly dispersed or non-uniformly dispersed over an upper surface of the detection layer. Typically, the semi-reflective islands are uniformly dispersed over an upper surface of the detection layer and have at least one dimension (i.e., length, width, or diameter) of at least about 1.0 micron (μm), desirably, from about 10.0 to about 100 μm; however, any semi-reflective island size, shape, and density may be used in the present invention. Further, the exposed areas typically have at least one dimension (i.e., length, width, or diameter) ranging from about 1.0 to about 100 μm; however, the exposed areas may have any dimensions in the present invention.

Figure 4:
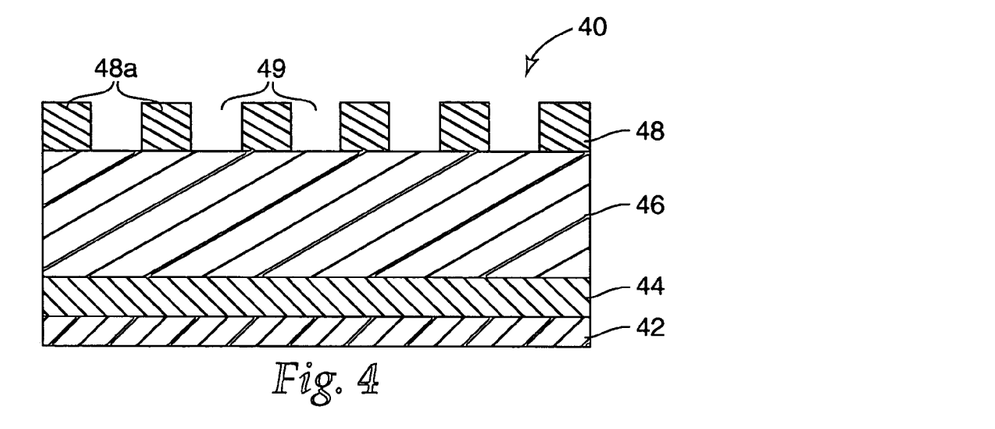
FIG. 4 depicts an exemplary multi-layered film of the present invention having a discontinuous semi-reflective layer.
Figure 5A:
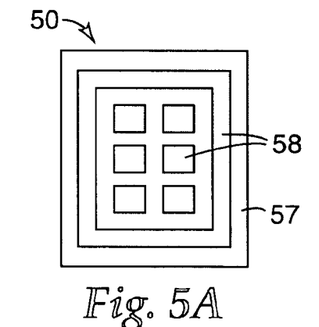
FIGS. 5A-5F depict frontal views of exemplary arrays of multi-layered film sensors of the present invention.
Figure 5B:
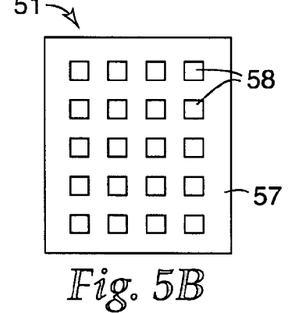
Figure 5C:
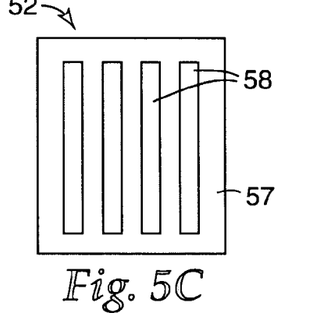
Figure 5D:
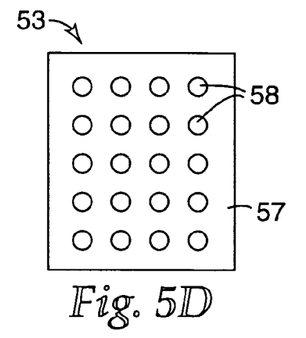
Figure 5E:
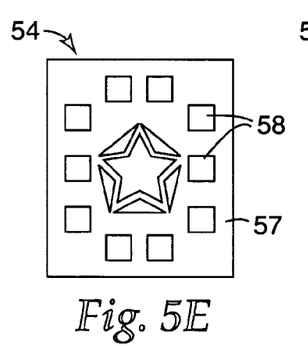
Figure 5F:
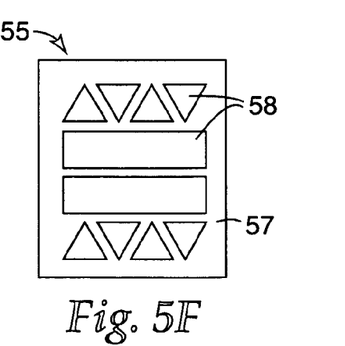

An exemplary multi-layered film of the present invention having a discontinuous semi-reflective layer is shown in FIG. 4. Exemplary multi-layered film sensor 40 comprises (optional) substrate layer 42, reflective layer 44, detection layer 46, and discontinuous semi-reflective layer 48 over detection layer 46. In this embodiment, discontinuous semi-reflective layer 48 comprises semi-reflective islands 48a and exposed areas 49 within a given plane above detection layer 46. Exposed areas 49 provide immediate access for an analyte to detection layer 46 without the need to permeating through a semi-reflective material. The degree of exposure of detection layer 46 may be controlled by varying one or more of the following parameters: the number of semi-reflective islands 48a per given area, and the size of each semi-reflective island 48a.

One suitable method for providing a discontinuous semi-reflective layer over a detection layer comprises laser ablation method as described in Example 11 below. Portions of the semi-reflective layer may be removed by exposing the portions to a laser as described in U.S. Pat. Nos. 6,180,318 and 6,396,616 assigned to 3M Innovative Properties Company (St. Paul, Minn.), the subject of which is hereby incorporated in its entirety. Another exemplary method that could be used to produce a discontinuous semi-reflective layer is a photo-imaging method.

In one desired embodiment of the present invention, the discontinuous semi-reflective layer comprises a number of semi-reflective islands uniformly dispersed over an upper surface of the detection layer, wherein each semi-reflective island has an upper surface area in the shape of a square or circle having a length, width, or diameter of at least about 1.0 μm, more desirably, from about 10.0 to about 100 μm. It should be understood that each semi-reflective island may have an upper surface area in a variety of shapes including, but not limited to, triangular, rectangular, star-shaped, diamond-shaped, etc., and one or more dimensions of at least about 1.0 μm, more desirably, from about 10.0 to about 100 μm. Further, it should be understood that each semi-reflective island may be either permeable or impermeable to one or more analytes. When the semi-reflective islands are permeable to one or more analytes, the colorimetric sensor allows one or more analytes to contact the detection layer directly through exposed areas, as well as indirectly through the semi-reflective islands.

Although not shown in FIG. 4, it should be noted that a laser ablation method (such as described in U.S. Pat. Nos. 6,180,318 and 6,396,616), a chemical etching method, or another method could be used to remove portions of the semi-reflective layer, as well as portions of the detection layer to form wells that extend from an upper surface of the semi-reflective layer into the detection layer, and possibly to an upper surface of the reflective layer (or an upper surface of the optional substrate). In this embodiment, the resulting structure comprises an array of multi-layered film islands (e.g., square islands having 100 µm sides within a grid of exposed areas having a width of about 10 µm) having the same detection layer composition and semi-reflective layer composition. The semi-reflective layer each island can be either permeable or impermeable to one or more analytes. When the semi-reflective islands are permeable to one or more analytes, the multilayer structures enable penetration of an analyte into the detection layer from the sides of the detection layer, as well as from the top of the detection layer. The size, shape and density of multi-layered film islands within the resulting structure may vary similarly to the semi-reflective islands described above. Typically, each multi-layered film island has one or more dimensions of at least about 1 µm such as about 10.0 to about 100 µm.

In addition to the above-described methods, multi-layered film islands may also be formed by depositing islands of detection layer material onto a reflective layer and then depositing a semi-reflective layer on top of each detection layer island. Various printing techniques including, but not limited to, ink-jet printing and contact printing, may be used to deposit the detection layer in island or patterned form onto a reflective layer.

In one desired embodiment of the present invention, the discontinuous semi-reflective layer comprises a single layer of semi-reflective islands over an upper surface of a detection layer, wherein the detection layer comprises at least one inorganic component. In a further desired embodiment, the discontinuous semi-reflective layer comprises a single layer of semi-reflective islands over an upper surface of a detection layer, wherein the detection layer comprises at least one inorganic component in combination with at least one polymer component. In yet a further desired embodiment, the discontinuous semi-reflective layer comprises a single layer of semi-reflective islands over an upper surface of a detection layer, wherein the detection layer comprises at least two different polymeric components, wherein the polymeric components are (1) blended with one another, (2) within a given layer but not blended with one another, (3) in a layer separate from one another, or (4) any combination of (1) to (3).

Additional Layers

The sensor film may comprise additional layers between any of the previously described layers, as long as the additional layer (or layers) does not interfere with the optics of the sensor film. Additional layers could include tie layers, structural layers, etc.

The sensor film may also include additional layers above the semi-reflective layer. Suitable additional layers that may at least partially cover the semi-reflective layer include, but are not limited to, a transparent layer or laminate, and a masking layer to temporarily or permanently shield a portion of the semi-reflective layer from exposure to one or more analytes. The additional layers may be applied directly onto the semi-reflective layer or may be temporarily or permanently bonded to the semi-reflective layer via a tie layer or other adhesive layer. If necessary, an outer surface of the semi-reflective layer may be treated (e.g., chemically etched or primed, electrical discharge treatment, etc.) to enhance the bond to additional layers.

In one exemplary embodiment, a masking layer is provided over the semi-reflective layer in the form of a pattern. In this embodiment, upon exposure to an analyte, the colorimetric sensor displays a signal in the form of a pattern (i.e., a reverse pattern of the masking layer on the semi-reflective layer). The signal pattern may have any desired configuration including, but not limited to, shapes, letters, words, a specific message to the user, safety instructions to the user, a company logo, etc.

Multi-Layered Film Configurations

The multi-layered films of the present invention may be used alone or may be part of a device for detecting the presence and/or concentration of one or more analytes. In one embodiment of the present invention, the multi-layered film sensor is at least partially enclosed by a housing. The housing desirably comprises at least one opening positioned above the semi-reflective layer so that the semi-reflective layer is viewable through the at least one opening. In some embodiments, the housing comprises at least one opening, wherein the at least one opening provides a restricted view of an upper surface of the semi-reflective layer so as to minimize any potential change in the viewable color of the sensor (and confusion of the user as to the sensor reading) due to the angle of view. Typically, the restricted view allows a view of the upper surface of the semi-reflective layer within an angle of ±30°, more desirably, ±15° from a normal view (i.e., a view from a position perpendicular to the outer surface of the semi-reflective layer).

The housing (or the optional substrate described above) may also be used to constrain the multi-layered film sensor of the present invention so that the film is in an arched or cylindrical shape. Such a configuration allows a user to view the sensor from a larger range of viewing angles with minimal shift in color.

As discussed above, the multi-layered film sensors of the present invention may possess a substantially continuous semi-reflective layer or a discontinuous semi-reflective layer. In one exemplary embodiment of the present invention, the colorimetric sensor comprises a substantially continuous reflective layer; a detection layer over the reflective layer, wherein the detection layer comprises (i) at least one polymer component, (ii) at least one inorganic component, or (iii) both (i) and (ii); and a substantially continuous semi-reflective layer over the detection layer, wherein the semi-reflective layer has an index of refraction different from the index of refraction of the detection layer and is permeable to a given analyte. Desirably, the substantially continuous reflective layer, the substantially continuous semi-reflective layer, or both, comprise a single layer of reflective or semi-reflective material to minimize the thickness of either or both layers so that one or more analytes can permeate either or both layers.

In a further exemplary embodiment of the present invention, the colorimetric sensor comprises a reflective layer; a detection layer over the reflective layer; and a discontinuous semi-reflective layer over the detection layer, wherein the semi-reflective layer has an index of refraction different from the index of refraction of the detection layer. In this exemplary embodiment, the sensor desirably possesses at least one of the following features:

(a) the discontinuous semi-reflective layer comprises a single layer of semi-reflective islands;

(b) the discontinuous semi-reflective layer comprises a single layer of semi-reflective islands having at least one dimension greater than 10 μm, and exposed areas between the semi-reflective islands, wherein the exposed areas have a width of at least 1.0 μm;

(c) the detection layer contains wells extending a depth into the detection layer;

(d) the detection layer comprises at least one inorganic component either alone or in combination with at least one polymer component;

(e) the detection layer comprises at least one inorganic component, wherein the at least one inorganic component is (i) blended with at least one polymer component, (ii) within a given layer containing at least one polymer component but not blended with the at least one polymer component, (iii) in a layer separate from a layer containing at least one polymer component, or (iv) any combination of (i) to (iii); and (f) the detection layer comprises at least two different polymeric components, wherein the polymeric components are (1) blended with one another, (2) within a given layer but not blended with one another, (3) in a layer separate from one another, or (4) any combination of (1) to (3).

Method of Making

The multi-layered films of the present invention can be created via methods such as the process described, e.g., in U.S. Pat. No. 5,877,895. The detection layers may also be made by spin-coating, solution coating, extrusion coating, or other suitable techniques known in the art. The detection layer may also be made by plasma deposition processes such as plasma polymerization. The reflective and semi-reflective layers may also be made by standard vapor coating techniques such as evaporation, sputtering, chemical vapor deposition (CVD), plasma deposition, or flame deposition. Another method for making the reflective and semi-reflective layers is plating out of solution.

Uses

The film sensors may be used in a system comprising the sensor, a light source, and, optionally, a means of monitoring the sensor for a change of color. The light source can be a natural or artificial light source. The monitoring can be done in a variety of ways. It could be done visually, with a photo-detector, or by other suitable means.

The analyte may be present in a vapor or liquid medium. For example, an analyte may be present in the atmosphere or in a liquid solvent. In either case, in many embodiments of the present invention, at least a portion of the analyte permeates through the semi-reflective layer of the film sensor to interact with the detection layer.

Two or more film sensors may be used together to form an array. The array may be in any suitable configuration. For example, an array may comprise two or more sensors side by side, or sensors may be attached to, or constructed on, opposite sides of a substrate. The sensors within a given array may be of the same type or may be different. Arrays of multi-layered film sensors would be useful for identification of analytes, based upon their unique response signatures from the array in aggregate, as opposed to only detecting the presence of a chemical agent.

Exemplary arrays of multi-layered film sensors are shown in FIGS. 5A-5F. Each of exemplary arrays 50-55 comprises a base layer 57 and multi-layered film stacks 58 on an upper surface of base layer 57. Base layer 57 may be a substrate layer or a reflective layer as described above. Multi-layered film stacks 58 within a given array may have identical or different chemical compositions. For example, two or more multi-layered film stacks 58 within a given array may have (i) different detection layer chemistries (and/or receptor types, e.g. calixarenes, peptides), (ii) different detection layer pore size distributions, (iii) different detection layer thicknesses within a given stack, or (iv) any combination of (i) to (iii), so as to detect the presence and/or concentration of one or more analytes in a given sample medium.

In one exemplary embodiment of the present invention, the array comprising two or more colorimetric sensors, wherein each colorimetric sensor in the array comprises a detection layer containing (i) at least one polymer component, (ii) at least one inorganic component, or (iii) both (i) and (ii). In some embodiments, each colorimetric sensor in the array shares a common reflective layer. In one desired embodiment, the array comprises two or more colorimetric sensors, wherein each colorimetric sensor in the array (a) shares a common reflective layer and (b) comprises a multi-layered film island comprising a stack of layers including (i) a detection layer with a detection layer composition and (ii) a semi-reflective layer with a semi-reflective layer composition. Desirably, the detection layer composition is similar for each colorimetric sensor in the array and the semi-reflective composition is similar for each colorimetric sensor in the array.

As shown in FIGS. 5A-5F, sensor arrays may be configured as one or more discrete sensor elements in a uniformly distributed manner (e.g., array 51), in a non-uniform manner (e.g., array 55), side by side (bar gauge type, etc.) (e.g., array 52), or any other configuration.

The film sensors of the present invention have many useful applications. They can be used, e.g., to detect a wide range of organic vapors. The sensors may be used to detect the presence and/or concentration of a given analyte within a solution or gas. Sensor arrays may be used to detect the presence and/or concentration of one or more analytes within a solution or gas. In one possible application, the multi-layered film sensors provide an overall color pattern to a user based on the interaction of a liquid or gas medium with the array, rather than on the interaction of a liquid or gas medium with a single sensor element.

Prior to use, the multi-layered film sensors of the present invention are substantially free of an analyte to be detected. The "unexposed" multi-layered film sensor prior to use typically either (i) displays a first color or (ii) is colorless when viewed through the semi-reflective layer. Upon exposure to one or more analytes to be detected, the "unexposed" multi-layered film sensor converts to an analyte-containing colorimetric sensor. The analyte-containing colorimetric sensor either (i) displays a second color that is different from the first color, (ii) undergoes a color change from a first color to a colorless condition, or (iii) undergoes a color change from a colorless condition to a color-containing condition.

Depending on the type of analyte being detected, the multi-layered film sensor of the present invention may contain or be substantially free of biological material between the reflective layer and the semi-reflective layer. As used herein, the term "biological material" is used to encompass molecular receptors such as peptides, glycopeptides, proteins, antibodies, enzymes, oligonucleotides, and nucleic acids.

Any of the above-described sensors and arrays of sensors may be used to detect one or more analytes in a given medium. In one exemplary method of detecting of analyte, the method detects the presence or absence of an analyte, wherein the method comprises providing a colorimetric sensor (or array of sensors), providing a light source, contacting the sensor (or array of sensors) with a medium that may contain an analyte, and monitoring the sensor (or array of sensors) for a change in optical properties. As discussed above, the medium may be a liquid or a gas. Further, the one or more analytes may permeate through the semi-reflective layer, the reflective layer, or both layers.

EXAMPLES

This invention may be illustrated by way of the following examples. Unless otherwise stated, the sensor film samples were viewed from an angle normal to the surface of the film. Other viewing angles may be used. The color observed can vary depending on the angle of observation.

Example 1

A multi-layered colorimetric sensor film was produced via the deposition method described in U.S. Pat. No. 5,877,895.

An aluminum reflective layer (100 nm) and polymeric detection layer (500 nm) were sequentially deposited upon a polyester substrate layer (50 µm) in a single pass (15.24 m/min) through a vacuum web system. The aluminum reflective layer was thermally evaporated by feeding 0.1587 cm diameter aluminum wire (Alcoa stock number 1199, Pittsburgh, Pa.) onto an electrically heated (7V, 1250 amp) evaporation bar at a feed rate of 225 mm/min. The polymeric detection layer (500 nm) was deposited followed by an electron beam cure of 6.9 W-Sec. The monomer composition was a 48.5/48.5/3 by weight mixture of lauryl acrylate (available from Sartomer, Exton, Pa.)/IRR214 (a proprietary hydrocarbon diacrylate, available from UCB Chemicals, Drogenbos, Belgium)/EBECRYL 170 (a phosphoric acid monoacrylate compound also available from UCB Chemicals). Chromium (Academy Precision Materials, Albuquerque, N. Mex.) was then sputtered (2.95 W/cm2 DC power at 2 mTorr Argon pressure), in a subsequent pass (15.24 m/min) through the vacuum web system, onto the cured detection layer, to give a 5 nm thick outer layer. The multi-layer sensor film had a green hue.

Sections of the multi-layered film (2.54 cm square) were affixed on glass slides and exposed for one minute to saturated vapors of various organic solvents in sealed jars. Within each jar, the multi-layered film was suspended within the headspace above the neat liquid analyte. As shown in Table 1, the exposures resulted in vivid, visually detectable color changes. In each case, the color changes were reversible upon removal from the solvent vapor within tens of seconds, restoring the original green hue. Responses were qualitatively reproducible, as repeat exposures produced the same color changes.

TABLE 1

Color Changes on Exposure to Various Compounds

| Solvent | Initial Color | Color After Exposure |
|---|---|---|
| Chloroform | Green | Red/Pink |
| Toluene | Green | Red/Pink |
| Pyridine | Green | Red/Pink |
| Ethanol | Green | Yellow |
| Acetone | Green | Red/Pink |
| Water | Green | Green |

Example 2

Visible reflectance spectra were taken of the multi-layered films before and after exposure to a range of solvent vapors. Film sections (2.54 cm square, from Example 1) were affixed on glass slides and exposed to saturated organic vapors within sealed jars. Once equilibrated, the exposed films were removed and covered immediately with glass cover slides to prevent vapor desorption. Reflectance spectra of the exposed materials were then taken using a diffuse reflectance UV-VIS spectrometer. For all organic vapors tested, substantial red-shifting of the reflectance maxima were observed upon analyte exposure. The reflectance maximum centered at 524 nm (before exposure), for instance, exhibits shifts to higher wavelengths (red shifts). The magnitudes of the shifts ranged from 22 nm (acetonitrile) to 116 nm (methylene chloride), as shown in Table 2. This example shows that the multi-layered colorimetric sensor films respond to organic vapors, exhibiting colorimetric shifts for halocarbons, arenes, alcohols, ketones, nitrites, and ethers. No shift was observed in the reflectance spectra on exposure to saturated water vapor. Even upon submerging films in liquid water, no color change was observed.

TABLE 2

Reflectance Maxima Wavelength Shifts Upon Exposure to Solvent Vapors

| Solvent | Wavelength Shift (nm) |
|---|---|
| Chloroform | 65 |
| Toluene | 62 |
| Methylene Chloride | 116 |
| Acetonitrile | 22 |
| Acetone | 28.5 |
| Ethanol | 29 |
| Diethyl Ether | 35 |
| Bromobenzene | 81 |
| 3-pentanol | 51 |
| 3-pentanone | 46 |
| Methyl Ethyl Ketone | 62 |
| Water | 0 |

Example 3

In an effort to gauge the response sensitivity to different analyte vapors, sensor film, made as described in Example 1, was exposed to analytes at a range of concentrations using a simple flow-through setup. Concentrations (as determined by partial pressures) were controlled by bath temperatures. Air was bubbled through neat liquid analytes, which were chilled using cold temperature baths to control the vapor pressure. Mixtures of solid carbon dioxide (dry ice) and 3-heptanone or ethylene glycol gave bath temperatures of −38° C. and −15° C. respectively. An ice water bath was used to give temperatures of 0° C. Vapor pressures for each analyte were calculated at these temperatures using data from the *Handbook of Vapor Pressure* (Yaws, C.L. Gulf Publishing: Houston, 1994). Each air/vapor stream was then flowed via a stainless steel cannula into a spetum-sealed vial containing the multi-layered film. The color changes of each film on exposure were monitored visually, and multiple observations were taken to ensure equilibrium.

Table 3 presents the responses as a function of concentration, with "green" indicating the unexposed film color, "pink" indicating response for saturated vapors, and "yellow" indicating an intermediate response. The results indicate the ability to determine analyte concentration, as well as the qualitative presence of the vapor using the colorimetric sensor films of this invention.

TABLE 3

Film Colors as a Function of Solvent Vapor Concentration

| Analyte | Concentration (torr) | Film Color (visual) |
|---|---|---|
| Chloroform | 5.1 | Green/Yellow |
| | 25 | Yellow/Yellow-pink |
| | 59 | Red/Pink |
| | 196 | Red/Pink |
| Acetone | 6.4 | Green |
| | 30 | Green/Yellow |
| | 69 | Yellow/Yellow-pink |
| | 230 | Red/Pink |
| Methylene Chloride | 15 | Green/Yellow |
| | 63 | Yellow-pink |
| | 141 | Red/Pink |
| | 430 | Red/Pink |
| Toluene | 0.37 | Green |
| | 2.4 | Yellow-pink |
| | 6.7 | Red/Pink |
| | 28 | Red/Pink |
| Bromobenzene | 0.028 | Green/Green-yellow |
| | 0.24 | Yellow-pink |
| | 0.79 | Red/Pink |
| | 4.2 | Red/Pink |

Example 4

Sensor film (from Example 1) was used to detect organic compounds in water. Submersion of the film within a solution of tetrahydrofuran (THF) in water (5% by volume) yielded a visual change in color from green to yellow. Submersion into a solution of acetone in water (25% by volume) produced a visible change in color from green to yellow-green. This example shows that the multi-layer colorimetric sensor films of this invention can detect the presence of organic compounds in water. No change in color was observed upon exposure of the film to plain water.

Example 5

Two multi-layered sensor films were prepared via spin-coating of the detection layers. The structures were the same, except for the polymer detection layers. To make each sensor film, an aluminum reflective layer (100 nm) was deposited by electron beam evaporation (2.5 nm/sec evaporation rate) in a batch system vacuum coater onto a 50 μm polyester substrate layer. Poly(styrene) and poly(methylmethacrylate) detection layers were each deposited onto one of the aluminum-coated substrates via spin-coating. The polymers were coated via toluene solutions at concentrations of 5% (w/w) and 9.4% (w/w) respectively. The spin-coating was carried out at 3500 rpm for 25 seconds. The resulting polymer thicknesses were 260 nm (poly(styrene)) and 500 nm (poly(methylmethacrylate)). Chromium layers (5 nm) were then deposited onto each polymeric surface via sputtering conditions identical to those in Example 1, to complete the multi-layered sensor film constructions. Exposure of the sensor films to saturated chloroform vapor yielded reversible color shifts from purple to blue (poly(styrene)) and from pink to light green (poly(methylmethacrylate)). Exposure of the films to toluene vapor caused a permanent loss of interference-based color, as indicated by the failure of the film to recover its original color upon removal from the analyte. Transmission electron microscopy (TEM) studies indicate that this irreversible change was caused by delamination of the aluminum layer from the rest of the stack. This example demonstrates the ability to create multi-layered colorimetric sensors by spin-coating. It also demonstrates that a permanent change in the appearance of a sensor of the invention can be realized by the appropriate selection of materials and processes used to make the sensors.

Example 6

Two different multi-layered films were constructed having the same general structure and composition as that described in Example 1 except that the detection layer thickness for Sample 6A was 500 nm, while the thickness was 650 nm for Sample 6B. Both films contained detection layers made via polymerization of lauryl acrylate/IRR214/EB170 mixtures, as in Example 1. Responses of the two films to a series of vapors are shown in Table 4. While neither individual sensor can identify every analyte (i.e., 6A does not distinguish between toluene and acetone and 6B does not distinguish between acetonitrile and acetone), the combined responses from both sensors are unique to each species tested. The utility of sensor arrays containing more than one unique multi-layered film for analyte identification is demonstrated by this example.

TABLE 4

Color Changes Upon Exposure to Various Solvents

| | 6A (500 nm thick detection layer) | | 6B (650 nm thick detection layer) | |
|---|---|---|---|---|
| Solvent | Initial | After Exposure | Initial | After Exposure |
| Acetonitrile | Green | Yellow | Red | Green |
| Toluene | Green | Red/Pink | Red | Brown/Red |
| Acetone | Green | Red/Pink | Red | Green |

Example 7

An array containing six different multi-layered films was used to obtain responses to a series of organic vapors: ethanol (EtOH), toluene (Tol.), acetone, acetonitrile, cyclohexane (CyHex), methylethylketone (MEK), methylene chloride ($CH_2Cl_2$), and tetrahydrofuran (THF). To prepare each sensor film, an aluminum reflective layer was first deposited by electron beam evaporation (2.5 nm/sec evaporation rate) in a batch system vacuum coater onto a 50 μm polyester substrate layer. Each sample was then spincoated with a polymeric material to produce detection layers as follows: Sample 7A Poly(α-methylstyrene)(Aldrich, 1,300 MW); Sample 7B poly(vinylphenol)(Polysciences, MW=1,500-7,000); Sample 7C poly(vinylpyrrolidone)(Aldrich, 55,000 MW); and Sample 7D poly(vinylalcohol)(Aldrich, 89% hydrolyzed, MW=85,000-141,000). Each polymeric sample was spincoated onto the aluminum sides of separate 1.5 inch×1.5 inch (3.8 cm×3.8 cm) sections of the aluminized polyester. The spin-coating was carried out at 3000 rpm for 1 minute, producing polymer film thicknesses of 500, 270, 250, and 290 nm, respectively. Chromium layers (5 nm) were then deposited onto each polymeric surface via sputtering conditions identical to those in Example 1 to complete each multi-layered film construction.

Samples 6A and 6B described in Example 6 were also used within the six-membered sensor array. Sections of each film were fixed on glass slides and then exposed to saturated vapors in sealed jars. The initial colors and colors upon vapor exposure are noted in Table 5.

While no individual sensor can distinguish every analyte (i.e., 7B does not distinguish between EtOH and Acetone), the composite responses from the six sensor array are unique to each species tested.

within the detection layer had a width of about 5 nm, and a depth of about 100 nm. A semi-reflective layer of Cr was then sputter coated as in Example 1 to provide a substantially continuous semi-reflective layer having a thickness of 5 nm.

TABLE 5

| | 7A | | 7B | | 7C | | 7D | | 6A | | 6B | |
|---|---|---|---|---|---|---|---|---|---|---|---|---|
| Vapor | Initial | Final | Initial | Final | Initial | Final | Initial | Final | Initial | Final | Initial | Final |
| EtOH | Blue | Blue | Purple Blue | Red | Purple Blue | Red Pink | Green Blue | Blue | Red | Green | Green | Yellow |
| Tol. | Blue | Silver* | Purple Blue | Purple Blue | Purple Blue | Purple Blue | Green Blue | Green Blue | Red | Orange Brown | Green | Red Pink |
| Acetone | Blue | Yellow Green | Purple Blue | Red | Purple Blue | Yellow Green | Green Blue | Blue | Red | Green | Green | Red Pink |
| Acetonitrile | Blue | Green Blue | Purple Blue | Yellow Red | Purple Blue | Yellow Red | Green Blue | Green Blue | Red | Green | Green | Yellow |
| CyHex | Blue | Silver* | Purple Blue | Purple Blue | Purple Blue | Purple Blue | Green Blue | Green Blue | Red | Green | Green | Red Pink |
| MEK | Blue | Purple | Purple Blue | Green | Purple Blue | Purple Blue | Green Blue | Green Blue | Red | Green | Green | Yellow Pink |
| $CH_2Cl_2$ | Blue | Silver* | Purple Blue | Purple Blue | Purple Blue | Green | Green Blue | Green Blue | Red | Orange Brown | Green | Red Pink |
| THF | Blue | Red Pink | Purple Blue | Red | Purple Blue | Purple Blue | Green Blue | Green Blue | Red | Orange Brown | Green | Red Pink |

*Silver denotes that delamination occurred

Example 8

Multi-layered films were constructed similarly to the method described in Example 5. Aluminized polyester was prepared via evaporative coating of a 100 nm Al layer onto the polyester substrate. A 10% (mass/volume) solution of poly (vinylalcohol)(Aldrich, 89% hydrolyzed, 85,000-141,000 MW) in water was spincoated (3000 rpm, 1 min.) onto a section of the aluminized polyester fixed on a glass slide. The three layer film was then sputter coated with a 5 nm thickness of Cr to complete the stack. A multilayer film containing a poly(vinylpyrrolidone)(Aldrich, 55,000 MW) detection layer was made in analogous fashion by spincoating from a 10% (mass/volume) ethanol solution.

Example 9

The poly(vinylalcohol) containing multi-layered film described in Example 8 was covered with patterned sections of 810 SCOTCH BRAND MAGIC tape from 3M Company, which were cut against a printed 3M logo template. The laminated multilayer film exhibited color change upon exposure to moisture. Color change occurred only in the unlaminated regions, causing the 3M logo to emerge.

Example 10

Multi-layered films were constructed similarly to the method described in Example 1 except "Cr islands" were applied to the polymeric detection layer instead of a continuous Cr layer. To apply the Cr islands, a screen was placed between the Cr source and the polymeric detection layer, and the Cr was then sputtered onto the screen and cured detection layer to provide Cr islands having a thickness of 5 nm, and a square shape having length of 100 mm. An oxygen plasma, in RIE mode, was used to etch the polymer between the Cr islands. During the etching process, the Cr islands were converted to a transparent $CrO_x$ coating. The resulting "wells"

Example 11

Multi-layered films were constructed similarly to the method described in Example 1. After applying the substantially continuous semi-reflective Cr layer, portions of the semi-reflective Cr layer were removed using a laser ablation procedure as described in U.S. Pat. No. 6,180,318 resulting in square shaped islands having a length of 100 μm. The dimensions of semi-transparent area removed were visible (i.e., the wells had a width of about 10 μm), but sufficiently small so as to produce a color change when exposed to an analyte.

Example 12

Multi-layered films were constructed similarly to the method described in Example 11 except that portions of the detection layer were also removed using the laser ablation procedure. The resulting multi-layered film islands had a square shape with a length of 100 μm. The islands were separated by wells having a width of 10 μm, and a depth of about 505 nm.

Various modifications and alterations of this invention will become apparent to those skilled in the art without departing from the scope and spirit of this invention and it should be understood that this invention is not to be unduly limited to the illustrative embodiments set forth herein.

What is claimed is:

1. A colorimetric sensor for measuring one or both of the presence and concentration of an analyte, said colorimetric sensor comprising:
    a reflective layer;
    a detection layer over the reflective layer, the detection layer comprising at least one polymer component, said detection layer being capable of a change in optical thickness upon exposure to the analyte; and
    a semi-reflective layer over the detection layer, the semi-reflective layer having an index of refraction different from the index of refraction of the detection layer, wherein at least a portion of (i) the semi-reflective layer, (ii) the reflective layer, or (iii) both (i) and (ii) is permeable to the analyte;

wherein the detection layer comprises a porous detection layer comprising at least one polymer having an intrinsic microporosity.

2. The colorimetric sensor of claim 1, wherein the reflective layer and the semi-reflective layer independently comprise a metal.

3. The colorimetric sensor of claim 1, wherein the semi-reflective layer has a differential permeability such that the semi-reflective layer has a higher analyte permeability at a first location on an upper surface of the semi-reflective layer and a lower analyte permeability at a second location on the upper surface.

4. The colorimetric sensor of claim 3, wherein the first and second locations form a pattern on the upper surface of the semi-reflective layer.

5. The colorimetric sensor of claim 1, wherein the detection layer comprises a pattern of wells beneath a lower surface of the semi-reflective layer and extending a depth into the detection layer.

6. The colorimetric sensor of claim 1, wherein the detection layer further comprises an inorganic material, said inorganic material being (i) blended with the at least one polymer component, (ii) within a given layer containing the at least one polymer component but not blended with the at least one polymer component, (iii) in a layer separate from the at least one polymer component, or (iv) any combination of (i) to (iii).

7. The colorimetric sensor of claim 1, wherein the sensor further comprises a masking layer over at least a portion of the semi-reflective layer, said masking layer preventing (i) exposure of at least a portion of the semi-reflective layer to an analyte, and (ii) an exposure signal from the portion of the semi-reflective layer covered by said masking layer.

8. The colorimetric sensor of claim 7, wherein the masking layer is provided as a pattern over at least a portion of the semi-reflective layer.

9. The colorimetric sensor of claim 1, wherein the detection layer comprises two or more polymer components and wherein the optical thickness of each polymer component changes in the presence of a different analyte.

10. The colorimetric sensor of claim 1, wherein the detection layer comprises at least two polymers and wherein the optical thickness of only one polymer changes in the presence of an analyte.

11. The colorimetric sensor of claim 10, wherein the at least two polymers are arranged such that a visible pattern forms when the sensor is exposed to the analyte.

12. The colorimetric sensor of claim 1, wherein the detection layer has a first thickness in a first location of the detection layer and a second thickness in a second location of the detection layer, said second thickness being different from said first thickness.

13. The colorimetric sensor of claim 1, wherein at least a portion of the reflective layer is permeable to said analyte.

14. The colorimetric sensor of claim 1, wherein said sensor is substantially free of said analyte, and either (i) displays a first color or (ii) is colorless when viewed through the semi-reflective layer.

15. The colorimetric sensor of claim 1, wherein said sensor is substantially free of biological material between said reflective layer and said semi-reflective layer.

16. The colorimetric sensor of claim 1, further comprising molecular receptors in the detection layer.

17. The colorimetric sensor of claim 16, wherein the molecular receptors are selected from the group consisting of calixarenes, cyclodextrins, dendritic polymers, carbon nanotubes, azacrowns, crown ethers, anion chelating agents containing Lewis acid functionality, organometallic metal complexes, porphyrins, metalloporphyrins, peptides, glycopeptides, proteins, antibodies, enzymes, oligonucleotides, nucleic acids, and combinations thereof.

18. An array comprising two or more of the colorimetric sensors of claim 1.

19. The array of claim 18, wherein at least two colorimetric sensors in the array have (i) different detection layer chemistries, (ii) different molecular receptors within separate detection layers, (iii) different detection layer pore size distributions, (iv) different detection layer thicknesses, or (v) any combination of (i) to (iv).

20. The array of claim 18, wherein each colorimetric sensor in the array shares a common reflective layer and comprises a multilayered film island comprising a stack of layers including (i) a detection layer with a detection layer composition and (ii) a semi-reflective layer with, a semi-reflective layer composition.

21. A device comprising:
the colorimetric sensor of claim 1, and
a housing at least partially enclosing the colorimetric sensor, wherein the housing comprises at least one opening positioned above the semi-reflective layer, said at least one opening providing a restricted view of an upper surface of the semi-reflective layer.

22. The device of claims 21, wherein the restricted view allows a view of the upper surface of the semi-reflective layer within art angle of ±30° from a normal view.

23. The colorimetric sensor of claim 1, wherein the reflective layer is a substantially continuous layer.

24. The colorimetric sensor of claim 1, wherein the detection layer further comprises an inorganic material.

25. The colorimetric sensor of claim 1, wherein the detection layer comprises at least two different polymeric components, wherein the polymeric components are (1) blended with one another, (2) within a given layer but not blended with one another, (3) in a layer separate from one another, or (4) any combination of (1) to (3).

26. The colorimetric sensor of claim 3, wherein the semi-reflective layer is a substantially continuous layer.

27. The colorimetric sensor of claim 1, wherein the semi-reflective layer is a substantially continuous layer, and the reflective layer is permeable to said analyte.

28. The array of claim 18, wherein at least one colorimetric sensor in the array comprises a molecular receptor in the detection layer of the at least one colorimetric sensor.

29. An array comprising two or more of the colorimetric sensors for measuring one or both of the presence and concentration of an analyte, said two or more colorimetric sensors each independently comprise:
a reflective layer;
a detection layer over the reflective layer, the detection layer comprising (i) at least one polymer component, (ii) at least one inorganic component, or (iii) both (i) and (ii); and
a semi-reflective layer over the detection layer, the semi-reflective layer having an index of refraction different from the index of refraction of the detection layer and being permeable to said analyte, said sensor being capable of a change in color upon exposure to said analyte;
wherein each of the two or more colorimetric sensors in the array shares a common reflective layer and comprises a multi-layered film island comprising a stack of layers including (i) a detection layer with a detection layer composition and (ii) a semi-reflective layer with a semi-reflective layer composition.

30. The array of claim 29, wherein each multi-layered film island comprises (i) the same detection layer composition and (ii) the same semi reflective layer composition.

31. A colorimetric sensor for measuring one or both of the presence and concentration of an analyte, said calorimetric sensor comprising:
   a reflective layer;
   a detection layer over the reflective layer, the detection layer comprising at least one polymer component; and
   a discontinuous semi-reflective layer over the detection layer, the semi-reflective layer having an index of refraction different from the index of refraction of the detection layer, said sensor being capable of a change in color upon exposure to the analyte,
   wherein the sensor has at least one of the following features:
   (a) the discontinuous semi-reflective layer comprises a single layer of semi-reflective islands having at least one dimension greater than 10 µm, and exposed areas between the semi-reflective islands, said exposed areas having a width of at least 1.0 µm;
   (b) the discontinuous semi-reflective layer comprises a single layer of semi-reflective islands and the detection layer contains wells extending a depth into the detection layer;
   (c) the discontinuous semi-reflective layer comprises a single layer of semi-reflective islands and the detection layer comprises at least one inorganic component in combination with at least one polymer component;
   (d) the detection layer comprises at least one inorganic component, wherein said at least one inorganic component is (i) blended with the at least one polymer component, (ii) within a given layer containing the at least one polymer component but not blended with the at least one polymer component, (iii) in a layer separate from a layer containing the at least one polymer component, or (iv) any combination of (i) to (iii); and
   (e) the detection layer comprises at least two different polymeric components, wherein the polymeric components are (1) blended wit one another, (2) within a given layer but not blended with one another, (3) in a layer separate from one another, or (4) any combination of (1) to (3).

32. The colorimetric sensor of claim 31, wherein the semi-reflective layer is a discontinuous layer comprising a single layer of semi-reflective islands having at least one dimension greater than 10 µm, and exposed areas between the semi-reflective islands, said exposed areas having a width of at least 1.0 µm.

33. The colorimetric sensor of claim 31, wherein the semi-reflective layer is a discontinuous layer comprising a single layer of semi-reflective islands, and the detection layer contains wells extending a depth into the detection layer.

34. The colorimetric sensor of claim 31, wherein the semi-reflective layer is a discontinuous layer comprising a single layer of semi-reflective islands, and the detection layer comprises an inorganic material.

35. The colorimetric sensor of claim 34, wherein said inorganic material (i) is blended with the at least one polymer component, (ii) is within a given layer containing the at least one polymer component but not blended with the at least one polymer component, (iii) is in a layer separate from the at least one polymer component, or (iv) any combination of (i) to (iii).

36. The colorimetric sensor of claim 31, wherein the semi-reflective layer is a discontinuous layer, and the detection layer comprises at least two different polymeric components, wherein the polymeric components are (1) blended with one another, (2) within a given layer but not blended with one another (3) in a layer separate from one another, or (4) any combination of(1) to (3).

37. An array comprising two or more of the colorimetric sensors of claim 31.

38. The array of claim 37, wherein each colorimetric sensor in the array shares a common reflective layer and comprises a multi-layered film island comprising a stack of layers including (i) a detection layer with a detection layer composition and (ii) a semi-reflective layer with a semi-reflective layer composition.

* * * * *

UNITED STATES PATENT AND TRADEMARK OFFICE
CERTIFICATE OF CORRECTION

Page 1 of 2

PATENT NO. : 7,449,146 B2
APPLICATION NO. : 10/807655
DATED : November 11, 2008
INVENTOR(S) : Neal A Rakow It is certified that error appears in the above-identified patent and that said Letters Patent is hereby corrected as shown below:

Title Page, Item (56) Page 2
Column 2 (Foreign Patent Documents); Line 7, Delete "WO 87/03837" and insert
-- WO 84/03837 --, therefor.

Column 1
Line 19; Delete "calorimetric" and insert -- colorimetric --, therefor.

Column 8
Line 24; Delete "vinyldimethylazalactone" and insert -- vinyldimethylazlactone --, therefor.

Column 9
Line 67; Delete "run" and insert -- nm --, therefor.

Column 18
Line 14 (Approx.); Delete "nitrites" and insert -- nitriles --, therefor.
Line 56; Delete "spetum-sealed" and insert -- septum-sealed --, therefor.

Column 21
Line 64; Delete "mm" and insert -- nm --, therefor.

Column 24
Line 17; In Claim 20, delete "multilayered" and insert -- multi-layered --, therefor.
Line 19; In Claim 20, after "with" delete ",".
Line 30; In Claim 22, delete "art" and insert -- an --, therefor.

Column 25
Line 31 (Approx.); In Claim 31, after "with" insert -- the --.
Line 32; In Claim 31, delete "the detection" and insert -- the discontinuous
semi-reflective --, therefor.

Signed and Sealed this
Fifteenth Day of March, 2011

David J. Kappos
*Director of the United States Patent and Trademark Office*

Column 26

Line 1; In Claim 31, delete "wit" and insert -- with --, therefor.

Line 31; In Claim 36, after "another" insert -- , --.